United States Patent [19]

Laba et al.

[11] Patent Number: 4,524,062

[45] Date of Patent: Jun. 18, 1985

[54] ANTIPERSPIRANT/DEODORANT STICK COMPOSITIONS

[75] Inventors: Dennis Laba, Middlesex; John J. Margres, Jr., Old Bridge; Kristin Burkhardt, Union, all of N.J.

[73] Assignee: Armour Pharmaceutical Company, Tuckahoe, N.Y.

[21] Appl. No.: 468,431

[22] Filed: Feb. 22, 1983

[51] Int. Cl.³ .................. A61K 7/32; A61K 7/34; A61K 7/38

[52] U.S. Cl. .................. 424/65; 424/DIG. 5; 424/66; 424/68; 514/723

[58] Field of Search ............. 424/65, DIG. 5, 68, 424/66

[56] References Cited

U.S. PATENT DOCUMENTS

| | | | |
|---|---|---|---|
| 1,984,669 | 12/1934 | Taub | 424/DIG. 5 |
| 2,732,327 | 1/1956 | Teller | 424/DIG. 5 |
| 2,970,083 | 1/1961 | Bell | 424/DIG. 5 |
| 3,978,207 | 8/1976 | Fotin et al. | 424/63 |
| 4,126,679 | 11/1978 | Davy et al. | 424/66 |
| 4,202,879 | 5/1980 | Shelton | 424/65 |
| 4,234,450 | 11/1980 | Hirayama et al. | 424/DIG. 5 |
| 4,265,878 | 5/1981 | Keil | 424/DIG. 5 |
| 4,332,763 | 6/1982 | Hempel et al. | 424/DIG. 5 |
| 4,414,200 | 11/1983 | Murphy et al. | 424/DIG. 5 |

FOREIGN PATENT DOCUMENTS

| | | | |
|---|---|---|---|
| 1115213 | 12/1981 | Canada | 424/DIG. 5 |
| 48006 | 6/1980 | Japan | 424/DIG. 5 |
| 2062466 | 5/1981 | United Kingdom | 424/DIG. 5 |

Primary Examiner—Dale R. Ore

[57] ABSTRACT

Antiperspirant/deodorant stick composition which comprises: a powdered antiperspirant agent the particles of which are enrobed in a coating material, contained in a cologne stick base.

10 Claims, No Drawings

ANTIPERSPIRANT/DEODORANT STICK COMPOSITIONS

BACKGROUND OF THE INVENTION

1. Field of the Invention

The present invention relates to an antiperspirant/deodorant composition in the form of a solid stick. More particularly, the present invention relates to a novel antiperspirant/deodorant composition that surprisingly combines desirable attributes of prior art preparations into a cosmetically elegant product which heretofore has been unattainable for the reason of incompatibility between the acidic antiperspirant ingredients and the alkaline solid stick base.

2. Description of the Prior Art

It has been known in the art for many years to prepare various cosmetic compositions, including deodorants and antiperspirants, in stick form. The various compositions prepared in stick form include wax-based sticks, stearyl alcohol-based suspension sticks, multiphase systems and pressed powder sticks. In still other compositions of the prior art, variations and modifications were imposed upon the types of compositions mentioned, such as strict particle size requirements of the active ingredients or substitution of gellants used.

Notwithstanding their desirable attributes the aforementioned sticks exhibit some drawbacks. The wax-based sticks employing a large amount of nonvolatile long-chain hydrocarbons tend to form a wax layer when applied to the skin and thereby prevent intimate contact between the antiperspirant ingredient contained therein and the body fluid. Stearyl alcohol based sticks consisting substantially of polydimethylcyclosiloxanes lack the desired cooling effect characteristic of the alcoholic cologne sticks. Production of multiphase systems, used primarily for preventing interaction between the inherent acidity of the antiperspirant salts and the inherent alkalinity of the base used as carrier, is energy- and time-intensive and the components in the finished product tend to bleed or leak causing destructive interaction between the phases. Pressed powder technology, though appropriate for cosmetic systems such as eyeliners and rouges, has been successfully employed in antiperspirant system because of the glazing or crusting effect found to exist when the product is used in normally wet areas such as the axilla.

The need is apparent for an antiperspirant/deodorant cosmetic stick that incorporates characteristics such as stick integrity, after-feel, payout properties, high degree of cosmetic elegance similar to that of a sodium stearate based cologne deodorant stick, lack of tackiness, ease of formulation that is not energy- and time-intensive, and is of one phase having incorporated therein both a deodorant and an antiperspirant.

SUMMARY OF THE INVENTION

The above-described and other requirements are met by the antiperspirant/deodorant stick composition of the present invention which comprise based on the total weight of the composition: a stable, homogenous mixture of about 5 to 25 weight percent of a powdered antiperspirant agent the particles of which are enrobed or coated with 4 to 25 weight percent of a material such as glycol stearate that is both insoluble in hydroalcoholic systems and inactive as a solvent for the antiperspirant agent; a cologne stick base comprising about 10 to 25 weight percent of a deodorant, such as sodium aluminum chlorhydroxy lactate, 5-chloro-2-(2,4-dichlorophenoxy)phenol sold under the name triclosan, 3,4,4-trichlorocarbanilide, cetyl pyridinium chloride or sodium lactate, about 25 to 40 weight percent of a cosmetically acceptable organic alcohol, and about 3 to 15 weight percent of a gelling agent, such as sodium stearate, and perfume.

Other ingredients, such as humectants and lubricants, such as stearyl alcohol and sorbitol may also be present to improve the esthetics of the formulation. Each of such ingredients may be present in the range of about 0 to 5 weight percent.

Such compositions produce a highly esthetic antiperspirant/deodorant in stick form suitable for application to the human axilla. In particular, the compositions have excellent drying characteristics, superior slip-feel, antiperspirant efficacy and good shelf life stability.

DETAILED DESCRIPTION OF THE INVENTION

The deodorant/antiperspirant stick composition of the present invention comprises: an antiperspirant agent, a coating material for the antiperspirant agent, a deodorant, and a cologne stick base. These essential elements as well as optional components and concentrations thereof and composition preparation are discussed in detail as follows:

| Concentration of Representative Ingredients | | |
|---|---|---|
| | Ingredient | % w/w |
| A, | CHLORACEL ® 40% solution | 20–40 |
| B, | Alcohol SDA-40 | 25–40 |
| C, | Sodium Stearate | 3–15 |
| D, | Sorbitol 70% | 0–5 |
| E, | Stearyl alcohol | 0–5 |
| F, | MICRO-DRY ® Ultrafine | 5–25 |
| G, | Glycol stearate | 4–25 |
| H, | Perfume | q.s. |

COMPOSITION PREPARATION

The composition may be prepared by various methods known in the cosmetic industry. In general, the ingredients of A through E are combined and heated to about 70° C. Separately, component F and G are blended at about 70° C. to obtain uniform coating of G on F. The two mixtures are then combined, blended together and cooled to about 60° C. Subsequently, ingredient H is added, mixed therewith and the preparation is cooled to about 55° C. At this temperature the composition is poured into stick containers and allowed to cool to room temperature.

THE ANTIPERSPIRANT

An important component of the composition is a particulate astringent antiperspirant compound to impart antiperspirant efficacy to the deodorant/antiperspirant stick composition of the present invention.

Any aluminum astringent antiperspirant salt or aluminum and/or zirconium astringent complex in particulate or powdered form can be employed. Such salts and complexes are well-known in the antiperspirant art. Salts useful as astringent antiperspirant salts or as components of astringent complexes include aluminum halides, aluminum hydroxyhalides, zirconyl oxyhalides, zirconyl hydroxyhalides, zirconium aluminum glycine comples, and mixtures thereof. A particularly preferred astringent is aluminum chlorohydrate in a micronized, free-flowing powder form in which a minimum of 99.0% of the particles pass through a 400 mesh screen, sold under the trade name MICRO-DRY ® ULTRA-FINE, by Reheis Chemical Company.

THE COATING MATERIAL

According to the novel approach of the present invention, it has been found that an acidic antiperspirant ingredient may be added to an alkaline stick base without experiencing chemical incompatibilities and resulting in deleterious interactions between the acidic and basic components. This has been accomplished by subjecting the antiperspirant agent to a molten material that is both insoluble in hydroalcoholic systems and inactive as a solvent for the antiperspirant agent. Such a material will enrobe or coat the solid antiperspirant particles and will prevent interaction between the particles and the remaining components of the composition. Glycol stearate has been found to perform effectively; however, other materials having the above-described properties may be used as well.

THE COLOGNE STICK

Cologne stick base or sodium stearate soap gel sticks are known and used for various cosmetic purposes. Such sticks are stable at normal temperature ranges within certain known proportions of sodium stearate, alcohol and water. Cologne stick base containing cosmetic preparations have a pleasant cooling effect and do not leave a greasy or waxy residue on the skin.

The cologne stick base used in the compositions of the present invention comprise sodium aluminum chlorhydroxy lactate, water, a cosmetically acceptable alcohol, and sodium stearate as the primary ingredients.

Sodium stearate functions as a gellant in the hydroalcoholic mixture of sodium aluminum chlorhydroxy lactate and alcohol. Sodium stearate as used in this invention denotes the sodium salt of a mixture of fatty acids of which stearic acid and palmitic acid predominate with relatively small proportions of closely related fatty acids.

For use in the hydroalcoholic mixture, ethyl alcohol is preferred; however, any cosmetically acceptable alcohol may also be used.

Sodium aluminum chlorhydroxy lactate used as a deodorant in the hydroalcoholic mixture may be substituted by 5-chlor-2-(2,4-dichloro phenoxy)phenol, 3,4,4-trichlorocarbanilide, cetyl pyridinium chloride or sodium lactate. We prefer to use, however, CHLORACEL ®, 40% solution, sold by Reheis Chemical Company, which is an aqueous solution of a sodium aluminum chlorhydroxy lactate derived from the complexation reaction of aluminum chlorhydroxide complex with lactic acid and subsequent partial neutralization with alkali. In this commercial product the ratio of complexing acid to aluminum has been so regulated as to result in minimal skin irritation or fabric destruction. Since CHLORACEL ® is a 40% w/w water solution, no water needs to be added to the system.

Optionally, ingredients such as perfumes, emollients or moisture retention agents may be incorporated in the compositions of the present invention. For example, sorbitol, glycerin, propylene glycol, polyethylene glycol 300 and 400, stearyl, cetyl or myristyl alcohol may be added to improve the esthetics of the stick composition.

The following specific examples will further illustrate the invention.

EXAMPLE 1

An antiperspirant/deodorant stick composition according to the present invention was made using the following procedure:

28 grams of glycol stearate was heated to 65° to obtain therein a fluid consistency. 28 gms of aluminum chlorohydrate powder was added, and the mixture stirred until all the aluminum chlorohydrate powder particles were coated with the fluid glycol stearate and a homogeneous pre-blend was obtained. This mixture was set aside and its temperatue kept at 65° C. to be used later in the procedure.

In a reaction vessel equipped with a condenser, a thermometer and an overhead Lightnin' mixer, 144 grams of CHLORACEL ® 40% w/w solution and 158 grams of Alcohol SDA-40 were mixed together with constant stirring and the mixture was heated to 65°-70° C. To the reaction vessel, 8 grams of a sorbitol solution was added and the mixture was stirred for about one minute, followed by the addition of 32 grams of sodium stearate. While maintaining the temperature at 65°-70° C., the mixture was stirred until complete dissolution of the sodium stearate was achieved, approximately 15 minutes, and a clear solution was obtained. 2 grams of stearyl alcohol was then added and mixing continued at the above temperature until the stearyl alcohol was dissolved. The mixture was then cooled to about 60° C. the pre-blend of aluminum chlorohydrate/glycol stearate was added, the mixture was stirred to homogeneity and cooled to about 56° C. A small amount of perfume was added, the mixture was cooled to about 54° C. and poured into suitable containers.

Following the process described in Example 1 the following antiperspirant/deodorant stick compositions were made:

EXAMPLES 2-6

| Components | Wt % | | | | |
| --- | --- | --- | --- | --- | --- |
| | 2 | 3 | 4 | 5 | 6 |
| CHLORACEL ® 40% Solution | 40% | 25% | 36% | 34% | 40% |
| Alcohol | 33 | 27 | 39 | 37 | 36 |
| Sodium Stearate | 9 | 15 | 4.5 | 14 | 10 |
| Stearyl Alcohol | — | 1 | — | — | 1 |
| Cetyl Alcohol | 0.5 | — | — | — | 0.5 |
| Sorbitol | 2 | 4 | — | — | — |
| Propylene Glycol | — | — | — | 2 | 2 |
| Aluminum Chlorohydrate | 8.5 | 15 | 10.5 | 7 | — |
| Aluminum-Zirconium Tetra chlorohydrex-Gly | — | — | — | — | 4.0 |
| Glycol Stearate | 7 | 13 | 10 | 5 | 7.5 |
| | 100% | 100% | 100% | 100% | 100% |

The antiperspirant/deodorant stick composition of the present invention is conveniently and easily applied as stick integrity allows it to retain its shape, renders a pleasant cooling effect to the skin without tackiness or unesthetic afterfeel and possesses quickdrying characteristics with excellent payout.

The present invention may be modified in light of the teaching of the disclosure without departing from the spirit or essential atributes thereof, all of which are within the scope of the invention which is to be measured by the appended claims read in the light of the specification.

What is claimed is:

1. A deodorant-antiperspirant stick composition comprising
   a, 5 to 25 weight percent of an antiperspirant agent of solid particles selected from the group consisting of aluminum halide, aluminum hydroxyhalide, zirconyl oxyhalide, zirconyl hydroxyhalide and zirconium aluminum glycine complex;
   b, 4 to 25 weight percent glycol stearate enrobing the solid particles of said antiperspirant agent and thereby forming coated antiperspirant particles;
   c, q.s. to 100 weight percent with a cologne stick base comprising the mixture of
      (1) 10 to 25 weight percent of a deodorant selected from the group consisting of sodium aluminum chlorhydroxy lactate, 5-chloro-2-(2,4-dichlorophenoxy)phenol, 3,4,4-trichlorocarbanilide, cetyl pyridinium chloride and sodium aluminum lactate,
      (2) 25 to 40 weight percent of a cosmetically acceptable alcohol, and
      (3) 3 to 15 weight percent of sodium stearate as gelling agent for said deodorant and alcohol mixture;
   said coated antiperspirant particles being suspended in said cologne stick base.

2. The compositin of claim 1 further comprising perfume.

3. The composition of claim 1 wherein said cosmetically acceptable alcohol is ethanol.

4. The composition of claim 1 wherein said cosmetically acceptable alcohol is isopropanol.

5. The composition of claim 1 wherein said antiperspirant agent is aluminum chlorohydrate.

6. The composition of claim 5 wherein said aluminum chlorohydrate is in a micronized free-flowing powder form in which at least 99.0% of the particles pass through a 400 mesh screen.

7. The composition of claim 1 further comprising a humectant.

8. The composition of claim 7 wherein said humectant is selected from the group consisting of sorbitol, glycerin, propylene glycol or polyethylene glycol.

9. The composition of claim 1 further comprising a lubricant.

10. The composition of claim 9 wherein said lubricant is cetyl alcohol or myristyl alcohol.

* * * * *